United States Patent [19]

Fridlender et al.

[11] 4,315,907

[45] Feb. 16, 1982

[54] COMBINED HETEROGENEOUS SPECIFIC BINDING ASSAY

[75] Inventors: Bertold Fridlender; Zohar Ben-Moyal, both of Jerusalem; Udi Olshevsky, Ramat-Gan; Regine Tirosh, Jerusalem, all of Israel

[73] Assignee: Ames-Yissum, Jerusalem, Ill.X

[21] Appl. No.: 89,269

[22] Filed: Oct. 29, 1979

[30] Foreign Application Priority Data

Oct. 30, 1978 [IL] Israel .................................... 551816

[51] Int. Cl.3 ...................... G01N 33/56; G01N 33/58

[52] U.S. Cl. ...................................... 424/1; 23/230 B; 422/61; 424/12; 435/7

[58] Field of Search .................... 421/1, 12; 23/230 B; 422/61; 435/7

[56] References Cited

U.S. PATENT DOCUMENTS 4,135,884 1/1979 Shen ........................................ 424/1
4,207,307 6/1980 Kaul et al. .............................. 424/1

FOREIGN PATENT DOCUMENTS 2015158 9/1979 United Kingdom ................. 23/915

*Primary Examiner*—Christine M. Nucker
*Attorney, Agent, or Firm*—Andrew L. Klawitter

[57] ABSTRACT

A heterogeneous specific binding assay method and test means for the simultaneous determination of each of a plurality of different ligands (e.g., antibodies, antigens or haptens) in a single liquid test sample. The assay may follow any conventional technique of a heterogeneous type, i.e., which includes a separation of a bound-species from a free-species form of the labeled reagent. The combined assay is accomplished by using solid-phase binding agents for the respective ligands to be determined which are differentially separable from each other, thereby permitting the use of a single label rather than a different label for each ligand to be determined. The assay is particularly suited to the simultaneous determination of different antibodies, particularly antibodies to different viral antigens, in a single serum sample.

37 Claims, No Drawings

COMBINED HETEROGENEOUS SPECIFIC BINDING ASSAY

BACKGROUND OF THE INVENTION

1. Field of the Invention

This invention relates to the quantitative determination of ligands, such as antibodies, antigens or haptens, in liquid media, including body fluids such as serum, based on specific binding assay techniques. In particular, the invention is directed to the detection of antibodies, antigens or haptens based on immunoassay techniques involving the use of labeled reagents, such as radiolabeled or enzyme-labeled reagents. The present invention provides a specific binding assay method of the heterogeneous type (i.e., wherein a bound-species of the labeled reagent is physically separated from a free-species thereof) for the simultaneous determination of each of a plurality of different ligands in a single liquid test sample.

2. Description of the Prior Art

A living system is able to detect, recognize and respond to the presence of foreign material (antigen) such as protein, virus, bacteria, and so forth, within that system. This response takes, inter alia, the form of producing an antibody specific for the particular antigen. There then occurs a specific reaction between the antibody and the antigen to form a complex. An antibody once produced is also capable of binding a hapten, i.e., a relatively small and simple compound which may be the determinant group of a given antigen, which hapten is capable of binding with the specific antibody but incapable itself of giving rise to the production of an antibody, unless it is bound to an antigenic carrier.

The binding interaction between an antigen or a hapten and its antibody is specific and sensitive. Other types of materials that participate in similar specific and sensitive binding interactions are enzymes and their substrates; materials such as hormones, vitamins, metabolites and pharmacological agents, and their receptors and binding substances; and other substances known in the science. These specific and sensitive binding reactions have given rise to a rapidly emerging analytical technique known as the specific binding assay technique. Where a radioactive label is used and the binding reaction involved is immunological, the method is known as a radioimmunoassay (RIA) method. Recently, several alternative labeling materials have been reported for replacement of radioisotopes, including enzymes, coenzymes, enzyme substrates, enzyme modulators such as inhibitors and allosteric effectors, fluorescent molecules, luminescent molecules, and others.

In conventional specific binding assay techniques, the test sample is combined with reagent means of various compositions that include a labeled binding agent having a monitorable label component and a binding component which participates with other constituents, if any, of the reagent means and with the ligand under determination to form a binding reaction system having two species or forms of the labeled binding agent, a bound-species and a free-species. The relative amount or proportion of the labeled binding agent that results in the bound-species compared to the free-species is a function of the presence (or amount) of the ligand to be detected in the sample.

As an illustration, a conventional competitive binding assay technique will now be described. In such a technique, the reagent means would comprise (1) a labeled binding agent in the form of the ligand to be detected (e.g., an antigen or hapten), such ligand constituting the binding component of the labeled agent, chemically linked to the label component (e.g., a radioactive atom or an enzyme) and (2) a solid-phase binding agent for the ligand (e.g., a solid-phase form of an antibody). Upon combination of the test sample and the reagent means, the ligand to be detected and the binding component of the labeled binding agent (in this illustration, a labeled form of the ligand) would compete in a substantially nondiscriminating manner for noncovalent binding to the solid-phase binding partner (in this illustration, an antibody). As a result, either the amount of labeled binding agent that would become bound to the binding partner (i.e., that results in the solid-phase bound-species) or that amount which would remain free (i.e., unbound to the binding partner and thus that results in the free-species) can be measured as a function of the amount of competing ligand present. The amount of labeled binding agent resulting in either species is determined by separating the solid-phase bound-species from the liquid-phase free-species and measuring, i.e., monitoring, the label component in one of the separated species.

As a further illustration, an alternative specific binding assay technique known as the "indirect solid-phase technique" will now be described. This type of assay is conventionally used where the ligand to be determined is a multi-valent entity such as antibodies. In the indirect solid-phase technique, the reagent means comprises (1) a labeled binding agent in the form of a binding partner (e.g., an antibody to an antibody) for the ligand to be detected (e.g., antibody) chemically linked to the label component, and (2) a solid-phase binding agent (e.g., an antigen corresponding to the antibody under assay bound to a solid-phase structure). The test sample is first incubated with the solid-phase binding agent whereby ligand from the sample becomes bound to the solid-phase binding agent, thus forming solid-phase ligand-binding agent complexes. Such complexes are then incubated with the labeled binding agent to form labeled solid-phase complexes (the bound-species) which are physically separated from the remaining liquid-phase (free-species) labeled binding agent. The amount of label associated with the solid-phase (bound-species) is a direct function of the amount of ligand in the test sample.

Attempts have been made to develop combined heterogeneous specific binding assays wherein a multiplicity of ligands are determined simultaneously in a single test sample. Such combined assay would result in a savings in time and cost over the performance of individual assays and would require a lesser volume of sample for assaying, which is an important consideration where the sample is a body fluid such as serum. Combined assays are of particular advantage where the assays are of a screening nature. An example would be the diagnosis of immunity of women to viruses and other antigens which are responsible for congenital malformations, such as Rubella, Cytomegalovirus, Herpes Simplex virus and the parasite toxoplasma. In a combined assay, the patient's immunity against two or more of these antigens, indicated by the presence of antibodies to such antigens in the serum of the patient, would be determined in a single test using a single serum sample. Such combined tests would be applied to wide-range immunological screening of women, e.g., at the earliest possible time during pregnancy or at a late stage of pregnancy as well as testing of both the mother and child after delivery. Such immunodiagnostic tests have hitherto been performed separately in respect of each of the above-mentioned antigens, each test requiring a separate sample of serum.

Several immunodiagnostic tests have been described for the separate detection and serological determination of Rubella virus specific antibodies and Cytomegalovirus (hereinafter "CMV") specific antibodies, including radioimmunoassay (RIA) and enzyme-immunoassay (EIA) tests. Voller and Bidwell [*Br. J. Exp. Path.* 56:338(1975) and 57:243(1976)] used enzyme-linked immunosorbent assay procedures for the separate determination of antibodies to Rubella and to CMV. In accordance with this procedure, polystyrene microplates coated with Rubella antigen were incubated with human serum containing Rubella antibody, followed by incubation with anti-(human globulin) labeled with alkaline phosphatase. The activity of the bound enzyme was measured colorimetrically.

U.S. Pat. No. 4,016,043 describes the determination of Rubella antibodies by forming, on a microtiter plate coated with Rubella antigen, a so-called "sandwich" consisting of the following sequence of layers: (solid-viral antigen)-antibody-(viral antigen-enzyme).

Kirsti et al [*J. Clin. Microbiol.* 4:117(1976)] describe an indirect solid-phase RIA procedure for detecting Rubella virus specific antibodies (IgG and IgM) in human serum. Purified Rubella virus was adsorbed onto polystyrene spheres and the antibodies which were bound to the virus after incubation with the serum were detected by subsequent binding of $^{125}$I-labeled anti-(human IgM) or anti-(human IgG). Similarly, Forghani et al [*J. Clin. Microbiol.* 4:470(1976)] used fixed, virus-infected cells as a source of antigen for binding the antibodies in the tested sera, while $^{125}$I-goat anti-(human IgG) was used for the detection of the specific antibodies (including Rubella antibody) which attached to the antigen. Similar indirect solid-phase RIA tests for CMV antibodies have recently been described by Forghani et al [*Infect. and Immunity* 14: 1184(1976)] and Knez et al [*J. Immunol.* 117:2006(1976)], the first using CMV-infected cells as the source of the antigen, and the other, viral soluble antigen fixed to microtiter plates. In both cases $^{125}$I-anti-(human globulin) was used for the detection of the antigen-antibody complexes formed.

In all of the above-described assays, a separate test specimen and separate assay procedure is necessary for determining each antibody. To the best of the applicants' knowledge, a combined specific binding assay for the simultaneous determination or more than one antibody species in a single sample was not known prior to their invention. [An assay similar to the present invention is reported in *J. Immunol. Methods* 26:381(1979) published after the filing date of applicants' priority Israel application.] However, certain attempts have been reported for developing combined heterogeneous specific binding assays in general.

U.S. Pat. Nos. 3,720,760 and 3,952,091 describe simultaneous multiple radioimmunoassays providing a qualitative indication of the presence of one or more of a specific group of antigens. The assays are merely simple "yes/no" screening tests which cannot distinguish one antigen from another and cannot provide quantitative results. If the test is positive, separate assays must then be performed in order to determine which particular antigen or antigens are in fact present (cf. col. 4, lines 56-64 in U.S. Pat. No. 3,720,760 and col. 1, lines 49-53 in U.S. Pat. No. 3,952,091).

Combined specific binding assays for related haptens using a different label for each hapten under assay are reported in U.S. Pat. No. 3,928,553 and *Acta Endocrinol.* 81:487-494(1976) for the thyroid hormones T-3 and T-4 and in German OLS No. 2,803,154 for vitamin B-12 and folate. A different type of label, i.e., $^{125}$I and $^{131}$I, is used for each of the haptens under assay. Such assays accordingly have the decided disadvantage of requiring separate or more involved instrumentation for measuring the several different labels necessary. A significantly more desirable combined assay would utilize the same label for all of the ligands under determination. Habermann et al in *J. Clin. Chem. Clin. Biochem.* 14:494-601(1976) describe a combined RIA procedure for T-3 and T-4 using the same label ($^{125}$I), however, a very complicated sequence of separation steps is required to isolate by column chromatography the labeled T-3 from labeled T-4 at the conclusion of the assay. A significantly more desirable combined assay would require no more than the conventional separation steps to isolate each labeled species from the others.

SUMMARY OF THE INVENTION

It has now been found that a combined heterogeneous specific binding assay using the same label for all of the ligands under determination simultaneously in a single test sample is possible by employing solid-phase binding agents corresponding to each ligand which are differentially separable. Thus, at the conclusion of the assay reaction each respective solid-phase is separated from the others (and from the remaining liquid-phase labeled binding agents) and the label measured in each as a function of the presence or amount of the respective ligand in the test sample.

Thus, in its broadest aspect, the present invention provides a specific binding assay method for the simultaneous determination of each of a plurality of different ligands in a single liquid test sample, comprising the steps of:

(a) combining said sample with reagent means for each different ligand to be determined, each such reagent means (i) including a labeled binding agent and a solid-phase binding agent, the label being the same for all such labeled binding agents included in the various reagent means combined with said sample, and the solid-phase binding agent for each different ligand to be determined being differentially separable from the other solid-phase binding agents for the other ligands to be determined, and (ii) forming with its corresponding ligand to be determined, a binding reaction system having a solid-phase bound-species and a free-species of its respective labeled binding agent, the amount of said label resulting in each resulting solid-phase bound-species being a function of the presence or amount of the corresponding ligand in said sample;

(b) separating each resulting solid-phase bound-species from the other solid-phase bound-species and from all of the remaining free-species; and (c) measuring the amount of label in each such separated solid-phase bound-species.

The labeled binding agent is preferably in the form of a labeled binding partner to all of the ligands under determination so that it binds equally to all such ligands. Using such preferred labeled binding agent, the complexes formed by binding of the various ligands to their respective solid-phase binding agents will be indiscriminantly labeled by binding of the labeled binding agent. This is shown illustratively as follows where $L_1, L_2, \ldots L_n$ are the plurality of different ligands to be determined, $\vdash B_1, \vdash B_2, \ldots \vdash B_n$ are the corresponding solid-phase binding agents, and BA* is the labeled binding agent capable of binding to all of $L_1$ through $L_n$:

Complex-forming reactions Labeling reactions

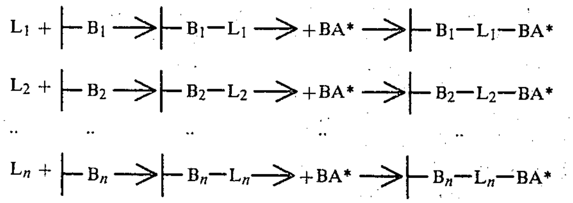

Thus, according to the preferred method, not only is a combined assay possible using a single type of label (signified by the asterisk in the above illustration) but also a single type of labeled binding agent is used (BA*) irrespective of the number of different ligands under determination.

This technique is particularly applicable to the simultaneous determination of each of a plurality of different antibodies in a single sample by the indirect solid-phase technique described hereinbefore. By different antibodies is meant antibodies against different antigens (e.g., antibodies against CMV antigen versus antibodies against Rubella antigen). Such preferred combined, indirect solid-phase antibody assay comprises the steps of:

(a) combining the sample with a plurality of differentially separable solid-phase carriers each having associated therewith an antigen specific for a different one of said antibodies to be determined, whereby each different antibody present in said sample becomes bound to its corresponding differentially separable solid-phase carrier through binding to the specific antigen associated with such carrier, thus forming solid-phase carrier-bound antibody complexes;

(b) combining the resulting solid-phase carrier-bound antibody complexes with an antibody incorporated with a label and capable of binding to any of said plurality of different antibodies to be determined, whereby said solid-phase carrier-bound antibody complexes become bound by said labeled antibody;

(c) separating each of said differentially separable solid-phase carriers from the other of such carriers and from all labeled antibody not bound to any of such carriers; and (d) measuring the respective amount of said label associated with each such separated solid-phase carriers.

The present invention also provides test means for the simultaneous determination of each of a plurality of different ligands in a single liquid test sample, comprising reagent means for each different ligand to be determined, each such reagent means (i) including a labeled binding agent and a solid-phase binding agent, the label being the same for all such labeled binding agents included in the various reagent means and the solid-phase binding agent for each different ligand to be determined being differentially separable from the other solid-phase binding agents for the other ligands to be determined, and (ii) forming with its corresponding ligand to be determined, a binding reaction system having a solid-phase bound-species and a free-species of its respective labeled binding agent, the amount of said label resulting in each resulting solid-phase bound-species being a function of the presence or amount of the corresponding ligand in said test sample.

DESCRIPTION OF THE PREFERRED EMBODIMENTS

Various techniques will be evident for designing differentially separable solid-phase binding agents in accordance with the present invention. For example, each respective solid-phase binding agent may comprise a single unitary solid-phase carrier having the binding agent associated therewith. Such solid-phase carriers suitable for use in the method according to the invention should be substantially solid and may assume any convenient shape, e.g., spheres, tubes, rods or strips. The carrier bodies should be of a material capable of being coated with the binding agent corresponding to the ligands to be assayed, the coating being effected in accordance with any of the covalent or noncovalent methods known for this end. Preferred carrier bodies according to the invention are polystyrene tubes, spheres or strips; these spheres or strips should preferably be of a size to fit into test tubes of the type conventionally used in immunoassay tests (e.g., about 75 mm in length and 12 mm in diameter). The carrier bodies to be used in each determination must be distinguishable from each other in order to identify the specific binding agent associated with each carrier body. This can be achieved by providing carrier bodies differing from each other in shape, size and/or color.

In accordance with a preferred embodiment of the invention, the vessel (e.g., the test tube) wherein the sample is incubated, serves as one of the carrier bodies coated with a binding agent. Thus, in accordance with this preferred embodiment, the inner surface of the vessel, or that part thereof which will come into contact with the sample, is coated by known methods, with one of the binding agents specific to the ligands to be assayed. In such a case, where the method is adapted for the simultaneous determination of only two ligands, the second binding agent (specific to the second ligand) may be coated on a polystyrene sphere which is subsequently placed into said vessel and the sphere need not carry any other identifying features. To add additional ligands to the assay one would select distinguishable carrier bodies for the corresponding additional binding agents required. Such additional carriers may be of distinguishable shape, size or color and should be of sizes to enable all to occupy the volume within the test tube which is in contact with the liquid reaction mixture.

In the last steps of the present method, the carrier bodies, to which the labeled complexes are linked, are separated from each other and a physical or chemical property (e.g., the radioactivity or enzymatic activity) of the label associated with each of the carrier bodies is measured separately by any of the well known methods conventionally used for such measurements. The values thus obtained may be compared with corresponding values obtained by submitting known positive and negative control samples, which contain (positive) or do not contain (negative) the specific ligand under assay, to an identical test procedure. The ratio of the label measurement for the sample under assay to that of the control sample may serve as a measure of the amount of the specific ligand contained in the sample under assay.

It is contemplated that the present assay may be applied to the detection of any ligand for which there is a specific binding partner. The ligand usually is a peptide, protein, carbohydrate, glycoprotein, steroid, or other organic molecule for which a specific binding partner exists in biological systems or can be synthesized. The ligand, in functional terms, is usually selected from the group consisting of antigens and antibodies thereto; haptens and antibodies thereto; and hormones, vitamins, metabolites and pharmacological agents, and their receptors and binding substances. Examples of ligands are immunologically-active polypeptides and proteins of molecular weights between 1,000 and 4,000,000, such as antibodies and antigenic polypeptides and proteins, as well as haptens of molecular weights between 100 and 1,500. Representative of such antigenic polypeptides are angiotensin I and II, C-peptide, oxytocin, vasopressin, neurophysin, gastrin, secretin, and glucagon. Representative of antigenic proteins are insulin, chorionic gonadotropin (e.g., HCG), carcinoembryonic antigen (CEA), myoglobin, hemoglobin, follicle stimulating hormone, human growth hormone, thyroid stimulating hormone (TSH), human placental lactogen, thyroxine binding globulin (TBG), intrinsic factor, transcobalamin, enzymes such as alkaline phosphatase and lactic dehydrogenase, and hepatitis-associated antigens such as hepatitis B surface antigen ($HB_sAg$), hepatitis B e antigen ($HB_eAg$) and hepatitis B core antigen ($HB_cAg$). Representative of antibody ligands are those antibodies of the IgG, IgE, IgM and IgA classes specific for any of the antigens or haptens herein described. The class of hapten ligands are exemplified by thyroxine, liothyronine, the estrogens such as estriol, prostaglandins, vitamins such as biotin, vitamin $B_{12}$, folic acid, vitamin E, vitamin A, and ascorbic acid (vitamin C), and drugs. The present invention is particularly suited to the determination of antibodies to viral antigens such as Rubella and CMV.

It is contemplated that any type of label presently known or hereafter discovered to be useful in specific binding assays can be used in the present invention. Preferred labels under the current state of the art are radioactive isotopes (e.g., $^{125}I$) and enzymes (e.g., phosphatase). All other parameters of the assay method are well within the ordinary skill in the art. In particular, the state of the art teaches allowable and preferred sample volumes and dilutions, incubation times and temperatures, methods for associating the respective binding agents with the solid-phase carriers either by covalent or noncovalent bonding, methods and instrumentation for measuring the label, and techniques for correlating assay results with standard values.

The reagent or test means of the present invention comprises all of the essential chemical elements required to conduct a desired assay method encompassed by the present invention. The test means is presented in a commercially packaged form, as a composition or admixture where the compatability of the reagents will allow, in a test device configuration, or as a test kit, i.e., a packaged combination of containers holding the necessary reagents. In its broadest aspect, the test means comprises reagent means for each different ligand to be determined, each such reagent means (i) including the labeled binding agent and the differentially separable solid-phase binding agent as described hereinabove and (ii) forming with its corresponding ligand to be determined, a binding reaction system having a solid-phase bound-species and a free-species as described hereinabove. Where, in accordance with a preferred embodiment described above, e.g., the combined, indirect solid-phase technique, the labeled binding agent is in the form of a labeled binding partner to all of the ligands under determination, obviously only one labeled binding agent is required for all of the respective reagent means. Thus, in such a case, the test means comprises such singular labeled binding agent and differentially separable solid-phase binding agents for each of the ligands under determination. Of course, in all embodiments, the reagent means can include other reagents as are known in the art and which may be desirable from a commercial and user standpoint, such as buffers, diluents, standards, and so forth.

As described in the examples which follow, a particularly preferred immunoassay test kit for the simultaneous determination of each of a plurality of different antibodies in a single sample of a liquid medium, comprising, in a packaged combination, (1) a plurality of differentially separable solid-phase carriers each having associated therewith an antigen specific for a different one of said antibodies to be determined; and (2) a container of an antibody incorporated with label and capable of binding to any of said plurality of different antibodies to be determined.

The present invention will now be illustrated, but is not intended to be limited, by the following examples.

TABLE OF CONTENTS FOR EXAMPLES

| Example No. | |
|---|---|
| 1 | Preparation of soluble CMV antigen |
| 2 | Preparation of soluble Rubella antigen |
| 3 | Preparation of solid-phase (coated tube) CMV antigen |
| 4 | Preparation of solid-phase (coated sphere) Rubella antigen |
| 5 | Preparation of radiolabeled ($^{125}I$) rabbit anti-human IgG |
| 6 | Determination of CMV and Rubella antibody titers by separate radioimmunoassays |
| 7 | Combined radioimmunoassay for CMV and Rubella antibodies |
| 8 | Determination of CMV and Rubella antibody titers by separate enzyme immunoassays |
| 9 | Combined enzyme immunoassay for CMV and Rubella antibodies |

EXAMPLE 1

Preparation of Soluble CMV Antigen

Human primary embryonic fibroblasts were grown as monolayers in roller bottles containing minimum essential medium and 10% fetal calf serum (Grand Island Biological Company, New York, N.Y., USA.). The cells were infected with CMV AD-169 strain (American Type Culture Collection, Rockville, Md., USA) at multiplicity of infection of 1 plaque forming unit (pfu) per cell. At the completion of the cytopathic effect, each roller bottle was washed with phosphate buffered saline (PBS) containing 0.8% sodium chloride, 0.02% potassium chloride, 0.115% dibasic sodium phosphate ($Na_2HPO_4$-$12H_2O$) and 0.02% monobasic potassium phosphate ($KH_2PO_4$) and the cells were scraped off the glass with glass beads, followed by pellet formation by centrifugation at 300 xg for 10 minutes. The supernatant liquid was removed and the precipitated pellet of the cells was resuspended in 10 milliliters (ml) of glycine buffer (containing 0.85% sodium chloride and 0.05 M glycine; pH adjusted to 9.0 by means of sodium hydroxide). The suspension of the cells was sonicated for 2 minutes and allowed to stand overnight at 4° C. The suspension was clarified by centrifugation at 7700 xg for 30 minutes, the soluble antigen remaining in the supernatant solution. This soluble antigen was stored at −70° C.

EXAMPLE 2

Preparation of Soluble Rubella Antigen

Baby hamster kidney-21-C13 cells (Flow Laboratories, Scotland) were grown in roller bottles containing Dulbeco's modified essential medium (DMEM) and 10% fetal calf serum (Grand Island Biological Co.) and infected with Rubella virus M-33 strain (American Type Culture Collection). Starting 48 hours after the infection, the bottles were harvested daily for a week. Cell debris was removed by low-speed centrifugation. Viral antigen was pelleted by centrifugation at 50,000 xg for one hour through a cushion of 20% weight per weight of sucrose in TNE buffer [containing 20 millimolar (mM) tris-(hydroxymethyl)aminomethane, 100 mM sodium chloride and 1 mM ethylenediamine tetracetic acid; pH 7.4]. The pellet thus formed was resuspended in TNE buffer and the suspension was sonicated until clear. The resuspended pellets were further purified in a 20–60% w/w sucrose gradient in TNE buffer by centrifuging at 38,000 rpm for two hours. The viral band obtained was aspirated and dialyzed to four hours at 4° C. against glycine buffered saline, pH 9 (described in Example 1). Thereafter glycerol was added to a final concentration of 5%. This Rubella antigen solution was stored frozen at −70° C.

EXAMPLE 3

Preparation of Solid-Phase (Coated Tube) CMV Antigen

The CMV soluble antigen obtained in Example 1 was diluted with glycine buffer (described in Example 1) to a concentration of 100–150 micrograms per milliliter (μg/ml) of protein and a complement fixation titer of $\frac{1}{4}$–$\frac{1}{8}$. Aliquots (0.2 ml) of this solution were accurately and carefully pipetted into the bottom of separate 12×75 mm polystyrene test tubes (from Ultraplast, Tel-Aviv, Israel) and the test tubes were incubated at 4° C. for 16 hours. At the end of the incubation, the liquid remaining in the test tubes was removed, the test tubes were dried in an air stream, sealed with parafilm (American Can Company, Connecticut, USA) and stored at 4° C.

EXAMPLE 4

Preparation of Solid-phase (Coated Sphere) Rubella Antigen

The optimal dilution of Rubella antigen to be used for coating the polystyrene spheres was determined by coating polystyrene test tubes of the type described in Example 3 above with a series of Rubella antigen dilutions ranging from 1:8 to 1:8000, using 0.2 ml of the diluted antigen solution for each test tube. Each coated tube was then incubated with 0.2 ml of serum containing Rubella antibody diluted 1:100 in PBS containing 1% of bovine serum albumin (BSA). Thereafter $^{125}$I-labeled anti-human IgG (Example 5 below) was added to each test tube and incubated therein. After separation of the liquid and washing, the radioactivity retained in each test tube was measured. In this manner it was found that in order to obtain the highest binding capacity for Rubella antibody, the test tubes should be coated with Rubella antigen solution at a dilution of about 1:150 to 1:300 in glycine buffer.

Polystyrene spheres $\frac{1}{4}$ inch in diameter (Precision Plastic Ball Co., Chicago, Ill., USA.) were washed with PBS and air dried on filter paper. The spheres were placed in a glass beaker and a solution of Rubella antigen diluted 1:200 with glycine buffer was added so as to cover all the spheres. The beaker with its contents were allowed to stand for 16 hours at 4° C., whereafter the liquid was decanted and the spheres were transferred onto a sheet of filter paper and air dried. The Rubella antigen-coated spheres were stored in sealed containers at 4° C.

If desired, the Rubella antigen-coated spheres may be treated with methanol in order to inactivate the virus while keeping the viral antigenic properties unchanged.

EXAMPLE 5

Preparation of Radiolabeled ($^{125}$I) Rabbit Anti-human IgG

The IgG fraction of rabbit anti-human IgG serum was obtained by passing the serum through a DEAE-cellulose column (DE-52, Whatman Ltd., England) equilibrated with 0.015 M potassium phosphate buffer, pH 8.0. The IgG fraction thus obtained was radioactively labeled with $^{125}$I by iodination in accordance with the chloramine T method described by Hutchinson and Zeigler, *Applied Microbiology*, December 1974, pp. 935–942.

EXAMPLE 6

Determination of CMV and Rubella Antibody Titers By Separate Radioimmunoassays In the present example, as well as in the following examples, four representative human sera were used for assaying CMV and Rubella antibodies. These four sera, which are designated A–D differ from each other in their titers of CMV and Rubella antibodies as follows:

| | Titer of Antibody to | |
|---|---|---|
| Serum Sample | CMV | Rubella |
| A | high | medium |
| B | medium | high |
| C | very low | medium |
| D | medium | low |

The titers of CMV and Rubella antibodies were predetermined in separate preliminary assays using the indirect solid-phase RIA procedure described below wherein each antigen was coated, as described above, on the interior surface of polystyrene test tubes. The procedure used was as follows:

1. The unknown serum sample or the control (negative) serum sample was diluted 100-fold in PBS containing 1% of BSA.

2. 200 μl of the diluted serum sample were accurately and carefully pipetted into the bottom of a test tube coated with the respective antigen (CMV antigen or Rubella antigen).

3. The test tube was incubated for 2 hours at 27° C. in a water bath. (In the case of CMV antigen, incubation for one hour was found to be sufficient).

4. At the end of the incubation the liquid in the test tube was removed by aspiration and the tube was washed twice with about 4 ml of PBS.

5. 200 μl of a solution of $^{125}$I-anti-human IgG [diluted with PBS containing 1% of BSA to a specific radioactivity of about 400–1000 counts per minute (cpm)/μl] were accurately and carefully pipetted into the bottom of the coated test tube.

6. The test tube was incubated for one hour at 37° C. in a water bath.

7. The liquid in the test tube was removed by aspiration and the test tube washed twice with about 4 ml of PBS.

8. The radioactivity retained by the test tube (the "bound-species") was measured by means of a gamma counter.

The relative antibody content of each serum sample in respect of CMV and Rubella antibodies was calculated as the ratio:

$$\frac{\text{cpm of serum sample}}{\text{cpm of negative (control) serum}}$$

The ratios so obtained are summarized in the following Table 1.

TABLE 1

| Serum Sample | CMV Antibody Ratios (RIA) (serum diluted 1:100) | Rubella Antibody Ratios (RIA) (serum diluted 1:100) |
|---|---|---|
| A | 6.03 | 2.5 |
| B | 2.86 | 4.25 |
| C | 1.03 | 2.5 |
| D | 2.23 | 1.2 |

The 100-fold dilution of the serum samples in step 1 above was somewhat arbitrary and was established as a result of titration curves obtained by two series of assays for CMV antibody and Rubella antibody, respectively, in order to determine in each case the so-called "end-point titration", which is defined as the highest dilution at which the cpm ratio between the unknown sample and the control sample is higher than 2. At the recommended 100-fold dilution, serum samples showing ratios of up to 1.5 should be considered as negative for the specific antibody under assay; samples showing ratios above 2.0 should be considered as positive for the antibody, whereas ratios between 1.5 to 2.0 should be considered as inconclusive and the test should be repeated at a lower dilution of the sample.

EXAMPLE 7

Combined Radioimmunoassay For CMV and Rubella Antibodies

Simultaneous determination of the titers of CMV antibody and Rubella antibody in the above described serum samples A–D, were carried out following the procedure of steps 1 to 7 described in Example 6, except that test tubes coated with CMV soluble antigen and containing a polystyrene sphere coated with Rubella antigen (such as described in Example 4) were used in each assay. After step 7 (Example 6) the polystyrene sphere coated with the Rubella antigen was removed from the test tube and transferred into a clean uncoated test tube. The radioactivity retained by the CMV antigen-coated test tube and by the polystyrene sphere coated with the Rubella antigen were determined separately by means of a gamma counter.

In two parallel series of control assays, exactly the same procedure was followed, except that in one series CMV antigen-coated test tubes containing an uncoated polystyrene sphere were used, and in the other series, uncoated test tubes each including a polystyrene sphere coated with Rubella antigen.

The results of these simultaneous assays are shown in Tables 2–5 below. These results demonstrate that the CMV and Rubella antibody titers determined in the simultaneous tests were practically identical with the corresponding values obtained in the control assays wherein each antibody was determined separately (Example 6).

TABLE 2

Serum A

| Serum Dilutions | Antigen Coated Onto Tube | Antigen Coated Onto Sphere | $^{125}$I-Retained By Tube (cpm) | $^{125}$I-Retained By Sphere (cpm) |
|---|---|---|---|---|
| 1:32 | — | Rubella | | 4213 |
| 1:128 | | | | 2610 |
| 1:512 | | | | 1527 |
| 1:2048 | | | | 718 |
| 1:8192 | | | | 435 |
| 1:32 | CMV | Rubella | 8900 | 3517 |
| 1:128 | | | 7800 | 2650 |
| 1:512 | | | 4700 | 1760 |
| 1:2048 | | | 1850 | 951 |
| 1:8192 | | | 850 | 511 |
| 1:32 | CMV | — | 9181 | |
| 1:128 | | | 7471 | |
| 1:512 | | | 4534 | |
| 1:2048 | | | 1979 | |
| 1:8192 | | | 912 | |

TABLE 3

Serum B

| Serum Dilutions | Antigen Coated Onto Tube | Antigen Coated Onto Sphere | $^{125}$I-Retained By Tube (cpm) | $^{125}$I-Retained By Sphere (cpm) |
|---|---|---|---|---|
| 1:32 | — | Rubella | | 5184 |
| 1:128 | | | | 4213 |
| 1:512 | | | | 3302 |
| 1:2048 | | | | 1955 |
| 1:8192 | | | | 900 |
| 1:32 | CMV | Rubella | 3520 | 4987 |
| 1:128 | | | 2680 | 4183 |
| 1:512 | | | 1610 | 3167 |
| 1:2048 | | | 902 | 2329 |
| 1:8192 | | | 620 | 921 |
| 1:32 | CMV | — | 3613 | |
| 1:128 | | | 2678 | |
| 1:512 | | | 1652 | |
| 1:2048 | | | 905 | |
| 1:8192 | | | 695 | |

TABLE 4

Serum C

| Serum Dilutions | Antigen Coated Onto Tube | Antigen Coated Onto Sphere | $^{125}$I-Retained By Tube (cpm) | $^{125}$I-Retained By Sphere (cpm) |
|---|---|---|---|---|
| 1:32 | — | Rubella | | 4373 |
| 1:128 | | | | 3391 |
| 1:512 | | | | 2042 |
| 1:2048 | | | | 1174 |
| 1:8192 | | | | 641 |
| 1:32 | CMV | Rubella | 1473 | 4773 |
| 1:128 | | | 1250 | 3137 |
| 1:512 | | | 870 | 2087 |
| 1:2048 | | | 685 | 1320 |

TABLE 4-continued

| Serum Dilutions | Serum C Antigen Coated Onto Tube | Sphere | $^{125}$I-Retained By Tube (cpm) | Sphere (cpm) |
|---|---|---|---|---|
| 1:8192 | | | 595 | 632 |
| 1:32 | CMV | — | 1573 | |
| 1:128 | | | 1314 | |
| 1:512 | | | 920 | |
| 1:2048 | | | 706 | |
| 1:8192 | | | 672 | |

TABLE 5

| Serum Dilutions | Serum D Antigen Coated Onto Tube | Sphere | $^{125}$I-Retained By Tube (cpm) | Sphere (cpm) |
|---|---|---|---|---|
| 1:32 | — | Rubella | | 2309 |
| 1:128 | | | | 1291 |
| 1:512 | | | | 768 |
| 1:2048 | | | | 480 |
| 1:8192 | | | | 160 |
| 1:32 | CMV | Rubella | 5176 | 2571 |
| 1:128 | | | 2035 | 1235 |
| 1:512 | | | 1485 | 742 |
| 1:2048 | | | 601 | 474 |
| 1:8192 | | | 457 | 328 |
| 1:32 | CMV | — | 4795 | |
| 1:128 | | | 2252 | |
| 1:512 | | | 1275 | |
| 1:2048 | | | 569 | |
| 1:8192 | | | 517 | |

EXAMPLE 8

Determination of CMV and Rubella Antibody Titers By Separate Enzyme Immunoassays The titers of CMV and Rubella antibodies in the four serum samples A–D described above were predetermined in separate preliminary assays using polystyrene test tubes coated with each antigen, as described above, by the following indirect solid-phase EIA procedure [the rabbit anti(human IgG) labeled with alkaline phosphatase was purchased from Miles-Yeda, Rehovot, Israel]:

1. The unknown serum sample or the control (negative) serum sample was diluted 100-fold in PBS containing 0.05% of Tween 20 (polyethylene sorbitan monolaurate, J. T. Baker, N.J., USA).

2. 200 μl of the diluted serum sample were accurately and carefully pipetted into the bottom of a test tube coated with the antigen (CMV antigen or Rubella antigen).

3. The test tube was incubated for 2 hours at 37° C. in a water bath. (In the case of CMV antigen, incubation for one hour was found to be sufficient).

4. At the end of the incubation the liquid in the test tube was removed by aspiration and the tube was washed twice with about 4 ml of PBS containing 0.05% of Tween 20.

5. 200 μl of a solution of alkaline phosphataseanti-(human IgG) in PBS containing 0.05% of Tween 20 were accurately and carefully pipetted into the bottom of the coated test tube.

6. The test tube was incubated for one hour at 37° C. in a water bath.

7. The liquid in the test tube was removed by aspiration and the test tube washed twice with about 4 ml of PBS containing 0.05% of Tween 20.

8. 1 ml of substrate solution (described hereinbelow) was added to the test tube.

9. The tube was incubated for one hour at 37° C. whereafter the enzymatic reaction was stopped by the addition of 30 μl of 10 N sodium hydroxide followed by vigorous mixing.

10. The optical density at 400–435 nm was measured.

The relative antibody content of each serum sample in respect of CMV and Rubella antibodies was calculated as the ratio:

$$\frac{O.D. \text{ of serum sample}}{O.D. \text{ of negative (control) sample}}$$

(O.D.=optical density at 400–435 nm)

The ratios thus obtained are summarized in the following Table 6.

TABLE 6

| Serum sample | CMV Antibody Ratio (EIA) (Serum diluted 1:100) | Rubella Antibody Ratio (EIA) (Serum diluted 1:100) |
|---|---|---|
| A | 25.2 | 3.73 |
| B | 5.1 | 4.43 |
| C | 1.5 | 2.82 |
| D | 10.6 | 1.5 |

If the purpose of the assay is merely for determining whether a particular antibody is present or absent in the serum sample, instead of measuring the optical density in step 10 above, a positive reaction may be scored qualitatively (or semiquantitatively) by the appearance of a yellow color which can be seen by the naked eye.

The substrate solution used in step 8 above was a 4-nitrophenyl phosphate solution in 10% diethanolamine buffer. One liter of this solution contains:

| | |
|---|---|
| 4-nitrophenyl phosphate | 1 g |
| Diethanolamine | 97 ml |
| Sodium Azide | 0.2 g |
| Hydrochloric Acid | 1 molar to give pH 9.8 |

As explained at the end of Example 6 above, the 100-fold dilution of the serum samples was established as a result of separate series of enzyme-immunoassays for each of the particular antibodies, wherein the "end-point titration" (defined in this case as the highest dilution at which the O.D. ratio between the unknown sample and the negative sample is higher than 2) for each of the antibodies was determined. As in the RIA case (Example 6) serum samples showing ratios of up to 1.5 should be considered as negative, those showing ratios above 2.0 should be considered as positive and those showing ratios between 1.5–2.0 should be considered as inconclusive and submitted to a repeated assay at a lower dilution.

EXAMPLE 9

Combined Enzyme Immunoassay for CMV and Rubella Antibodies

CMV and Rubella antibody titers were determined simultaneously in each of the above described sera A–D using the indirect solid-phase EIA technique. The procedure described in steps 1–7 of Example 8 was followed, except that in step 2 a polystyrene test tube coated with CMV soluble antigen and containing a ¼ inch diameter polystyrene sphere coated with Rubella antigen (as described in Example 4) was used. After step 7, the Rubella antigen-coated sphere was removed from the CMV antigen-coated test tube and transferred into a clean test tube. Steps 8, 9 and 10 of the procedure described in Example 8 were then carried out separately, with the CMV antigen-coated test tube on the one hand and with the uncoated test tube containing the Rubella antigen -coated sphere on the other hand.

Two series of control assays were carried out under identical conditions, one with CMV antigen-coated test tubes containing an uncoated polystyrene sphere and the other with Rubella antigen-coated polystyrene spheres placed in uncoated test tubes.

The results of all the assays are summarized in the following Tables 8-11.

TABLE 8

Serum A

| Serum Dilutions | Antigen Coated Onto: Tube | Antigen Coated Onto: Sphere | Enzyme Activity: Tube (O.D.) | Enzyme Activity: Sphere (O.D.) |
|---|---|---|---|---|
| 1:32 | — | Rubella | | 0.235 |
| 1:128 | | | | 0.250 |
| 1:512 | | | | 0.107 |
| 1:2048 | | | | 0.019 |
| 1:8192 | | | | — |
| 1:32 | CMV | Rubella | 1.217 | 0.261 |
| 1:128 | | | 0.935 | 0.255 |
| 1:512 | | | 0.487 | 0.124 |
| 1:2048 | | | 0.120 | 0.072 |
| 1:8192 | | | 0.035 | 0.049 |
| 1:32 | CMV | — | 1.107 | |
| 1:128 | | | 0.895 | |
| 1:512 | | | 0.594 | |
| 1:2048 | | | 0.101 | |
| 1:8192 | | | 0.047 | |

TABLE 9

Serum B

| Serum Dilutions | Antigen Coated Onto: Tube | Antigen Coated Onto: Sphere | Enzyme Activity: Tube (O.D.) | Enzyme Activity: Sphere (O.D.) |
|---|---|---|---|---|
| 1:32 | — | Rubella | | 0.293 |
| 1:128 | | | | 0.283 |
| 1:512 | | | | 0.209 |
| 1:2048 | | | | 0.007 |
| 1:8192 | | | | 0.015 |
| 1:32 | CMV | Rubella | 1.095 | 0.310 |
| 1:128 | | | 0.345 | 0.333 |
| 1:512 | | | 0.095 | 0.232 |
| 1:2048 | | | 0.050 | 0.085 |
| 1:8192 | | | 0.041 | 0.039 |
| 1:32 | CMV | — | 1.170 | |
| 1:128 | | | 0.369 | |
| 1:512 | | | 0.111 | |
| 1:2048 | | | 0.070 | |
| 1:8192 | | | 0.043 | |

TABLE 10

Serum C

| Serum Dilutions | Antigen Coated Onto: Tube | Antigen Coated Onto: Sphere | Enzyme Activity: Tube | Enzyme Activity: Sphere |
|---|---|---|---|---|
| 1:32 | — | Rubella | | 0.353 |
| 1:128 | | | | 0.250 |
| 1:512 | | | | 0.082 |
| 1:2048 | | | | 0.023 |
| 1:8192 | | | | 0.029 |
| 1:32 | CMV | Rubella | 0.053 | 0.274 |
| 1:128 | | | 0.030 | 0.224 |
| 1:512 | | | 0.010 | 0.079 |
| 1:2048 | | | 0.015 | 0.009 |
| 1:8192 | | | 0.003 | 0.039 |
| 1:32 | CMV | — | 0.061 | |
| 1:128 | | | 0.029 | |

TABLE 10-continued

Serum C

| Serum Dilutions | Antigen Coated Onto: Tube | Antigen Coated Onto: Sphere | Enzyme Activity: Tube | Enzyme Activity: Sphere |
|---|---|---|---|---|
| 1:512 | | | 0.015 | |
| 1:2048 | | | 0.015 | |
| 1:8192 | | | 0.037 | |

TABLE 11

Serum D

| Serum Dilutions | Antigen Coated Onto: Tube | Antigen Coated Onto: Sphere | Enzyme Activity: Tube (O.D.) | Enzyme Activity: Sphere (O.D.) |
|---|---|---|---|---|
| 1:32 | — | Rubella | | 0.169 |
| 1:128 | | | | 0.12 |
| 1:512 | | | | 0.059 |
| 1:2048 | | | | 0.037 |
| 1:8192 | | | | 0.015 |
| 1:32 | CMV | Rubella | 1.58 | 0.232 |
| 1:128 | | | 0.95 | 0.143 |
| 1:512 | | | 0.33 | 0.114 |
| 1:2048 | | | 0.12 | 0.053 |
| 1:8192 | | | 0.09 | 0.005 |
| 1:32 | CMV | — | 1.670 | |
| 1:128 | | | 0.929 | |
| 1:512 | | | 0.349 | |
| 1:2048 | | | 0.119 | |
| 1:8192 | | | 0.133 | |

It follows from the above results that CMV and Rubella antibody titers can be reliably determined quantatively in a simultaneous manner in a single assay, since the values of the optical density obtained in the above described simultaneous assays are practically identical to the corresponding values obtained separately in the control assays.

What is claimed is:

1. A specific binding assay method for the simultaneous determination of each of a plurality of different ligands in a single liquid test sample, comprising the steps of:

(a) forming a single reaction mixture comprising said sample and, corresponding to each different ligand to be determined, a labeled binding agent and a solid-phase binding agent, the label being the same for all such labeled binding agents and the solid-phase binding agent for each different ligand to be determined being differentially separable from the other solid-phase binding agents for the other ligands to be determined, whereby there is formed in said single reaction mixture, for each corresponding ligand to be determined, a binding reaction system having a solid-phase bound-species and a free-species of its respective labeled binding agent, the amount of said label resulting in each resulting solid-phase bound-species being a function of the presence or amount of the corresponding ligand in said sample;

(b) separating each resulting solid-phase bound-species from the other solid-phase bound-species and from all of the remaining free-species;

(c) measuring the amount of label in each such separated solid-phase bound-species; and (d) relating each such measured amount of label to the presence or amount of each of the corresponding different ligands in said sample.

2. The method of claim 1 wherein each respective solid-phase binding agent comprises a single unitary solid-phase carrier having said binding agent associated therewith.

3. The method of claim 2 wherein one of said respective solid-phase carriers is a vessel and said binding agent is bound to at least a portion of the interior surface thereof.

4. The method of claim 3 wherein the remainder of said respective solid-phase carriers are shaped bodies of sizes which enable all to be contained together within said vessel and each of which shaped bodies has bound thereto a respective binding agent.

5. The method of claim 1 wherein said label is a radioactive isotope.

6. The method of claim 1 wherein said label is an enzyme.

7. The method of claim 1 wherein said ligands to be detected are selected from any of the following classes of substances: antigens or antibodies thereto; haptens or antibodies thereto; or hormones, vitamins, or drugs, or receptors or binding substances therefor.

8. A specific binding assay method for the simultaneous determination of each of a plurality of different ligands in a single liquid test sample, comprising the steps of:

(a) forming a single reaction mixture comprising said sample and, corresponding to each different ligand to be determined, a labeled binding agent capable of binding to the respective ligand to be determined and a solid-phase binding agent also capable of binding to such respective ligand, the label being the same for all such labeled binding agents and the solid-phase binding agent for each different ligand to be determined being differentially separable from the other solid-phase binding agents for the other ligands to be determined, whereby there is formed in said single reaction mixture, for each corresponding ligand to be determined, a binding reaction system having a solid-phase bound-species comprising the respective labeled binding agent and the respective solid-phase binding agent both bound to the corresponding ligand to be determined, and said binding reaction system also having a free-species of its respective labeled binding agent, the amount of said label resulting in each resulting solid-phase bound-species being a function of the presence or amount of the corresponding ligand in said sample;

(b) separating each resulting solid-phase bound-species from the other solid-phase bound-species and from all of the remaining free-species;

(c) measuring the amount of label in each such separated solid-phase bound-species; and (d) relating each such measured amount of label to the presence or amount of each of the corresponding different ligands in said sample.

9. The method of claim 8 wherein each respective solid-phase binding agent comprises a single unitary solid-phase carrier having said binding agent associated therewith.

10. The method of claim 9 wherein one of said respective solid-phase carriers is a vessel and said binding agent is bound to at least a portion of the interior surface thereof.

11. The method of claim 10 wherein the remainder of said respective solid-phase carriers are shaped bodies of sizes which enable all to be contained together within said vessel and each of which shaped bodies has bound thereto a respective binding agent.

12. The method of claim 8 wherein said label is a radioactive isotope.

13. The method of claim 8 wherein said label is an enzyme.

14. The method of claim 8 wherein said ligands to be detected are selected from any of the following classes of substances: antigens or antibodies thereto; haptens or antibodies thereto; or hormones, vitamins, or drugs, or receptors or binding substances therefor.

15. An immunoassay method for the simultaneous determination of each of a plurality of different antibodies in a single sample of a liquid medium, comprising the steps of:

(a) forming a single reaction mixture comprising said sample and a plurality of differentially separable solid-phase carriers each having associated therewith an antigen specific for a different one of said antibodies to be determined, whereby each different antibody present in said sample becomes bound to its corresponding differentially separable solid-phase carrier through binding to the specific antigen associated with such carrier, thus forming solid-phase carrier-bound antibody complexes;

(b) combining the resulting solid-phase carrier-bound antibody complexes with an antibody incorporated with a label and capable of binding to any of said plurality of different antibodies to be determined, whereby said solid-phase carrier-bound antibody complexes become bound by said labeled antibody;

(c) separating each of said differentially separable solid-phase carriers from the other of such carriers and from all labeled antibody not bound to any of such carriers;

(d) measuring the respective amount of said label associated with each such separated solid-phase carriers; and (e) relating each such measured amount of label to the presence or amount of each of the corresponding different antibodies in said sample.

16. The method of claim 15 wherein one of said solid-phase carriers is a vessel and said specific antigen is bound to at least a portion of the interior surface thereof.

17. The method of claim 16 wherein the remainder of said respective solid-phase carriers are shaped bodies of sizes which enable all to be contained together within said vessel and each of which shaped bodies has bound thereto a respective antigen.

18. The method of claim 15 wherein said antibodies to be determined are different human gammaglobulin antibodies.

19. The method of claim 18 wherein said labeled antibody is a labeled form of anti-(human gammaglobulin).

20. The method of claim 19 wherein said antibodies to be determined are human gammaglobulin antibodies to cytomegalovirus and rubella respectively.

21. The method of any of claims 15, 19 and 20 wherein said label is a radioactive isotope.

22. The method of any of claims 15, 19 and 20 wherein said label is an enzyme.

23. Test means for the simultaneous determination of each of a plurality of different ligands in a single liquid test sample, comprising, for each different ligand to be determined, a labeled binding agent and a solid-phase binding agent, the label being the same for all such labeled binding agents and the solid-phase binding agent for each different ligand to be determined being differentially separable from the other solid-phase binding agents for the other ligands to be determined, which binding agents form, with each corresponding ligand to be determined, a binding reaction system having a solid-phase bound-species and a free-species of its respective labeled binding agent, the amount of said label resulting in each resulting solid-phase bound-species being a function of the presence or amount of the corresponding ligand in said test sample.

24. The test means of claim 23 wherein each respective solid-phase binding agent comprises a single unitary solid-phase carrier having said binding agent associated therewith.

25. The test means of claim 24 wherein one of said respective solid-phase carriers is a vessel and said binding agent is bound to at least a portion of the interior surface thereof.

26. The test means of claim 25 wherein the remainder of said respective solid-phase carriers are shaped bodies of sizes which enable all to be contained together within said vessel and each of which shaped bodies has bound thereto a respective binding agent.

27. The test means of claim 23 wherein said label is a radioactive isotope.

28. The test means of claim 23 wherein said label is an enzyme.

29. The test means of claim 23 wherein said ligands to be detected are selected from any of the following classes of substances: antigens or antibodies thereto; haptens or antibodies thereto; or hormones, vitamins, or drugs, or receptors or binding substances therefor.

30. An immunoassay test kit for the simultaneous determination of each of a plurality of different antibodies in a single sample of a liquid medium, comprising, in a packaged combination, (1) a plurality of differentially separable solid-phase carriers each having associated therewith an antigen specific for a different one of said antibodies to be determined; and (2) a container of an antibody incorporated with a label and capable of binding to any of said plurality of different antibodies to be determined.

31. The test kit of claim 30 wherein one of said solid-phase carrier is a vessel and said specific antigen is bound to at least a portion of the interior surface thereof.

32. The test kit of claim 31 wherein the remainder of said respective solid-phase carriers are shaped bodies of sizes which enable all to be contained together within said vessel and each of which shaped bodies has bound thereto a respective antigen.

33. The test kit of claim 30 wherein said antibodies to be determined are different human gammaglobulin antibodies.

34. The test kit of claim 33 wherein said labeled antibody is a labeled form of anti-(human gammaglobulin).

35. The test kit of claim 34 wherein said antibodies to be determined are human gammaglobulin antibodies to cytomegalovirus and rubella respectively.

36. The test kit of claim 30, 33 or 34 wherein said label is a radioactive isotope.

37. The test kit of claims 30, 33 or 34 wherein said label is an enzyme.

* * * * *